United States Patent [19]

Nagel

[11] 4,316,010

[45] Feb. 16, 1982

[54] CIS-$C_3''C_4''$-CARBONATE DERIVATIVES OF O-DEMETHYLOLEANDOMYCIN AND INTERMEDIATES THEREFOR

[75] Inventor: Arthur A. Nagel, Gales Ferry, Conn.

[73] Assignee: Pfizer Inc., New York, N.Y.

[21] Appl. No.: 222,187

[22] Filed: Jan. 2, 1981

[51] Int. Cl.$^3$ ............................................. C07H 17/08
[52] U.S. Cl. ........................................ 536/9; 424/180
[58] Field of Search ....................... 536/9, 17; 424/180

[56] References Cited

U.S. PATENT DOCUMENTS 4,133,950 1/1979 Myers ................................... 536/17
4,140,848 2/1979 Myers ..................................... 536/9

OTHER PUBLICATIONS

W. D. Celmer, Pure and Applied Chemistry 28: 413–453, (1971).

*Primary Examiner*—Blondel Hazel
*Attorney, Agent, or Firm*—Charles J. Knuth; Peter C. Richardson; Albert E. Frost

[57] ABSTRACT

Oleandomycin-Y(O-demethyloleandomycin), a by-product in the production of oleandomycin by fermentation, is converted through a series of intermediates into more useful cis-$C_3''$,$C_4''$-carbonate derivatives which have antibacterial activity much enhanced over that of oleandomycin-Y.

13 Claims, No Drawings

CIS-C$_3''$C$_4''$-CARBONATE DERIVATIVES OF O-DEMETHYLOLEANDOMYCIN AND INTERMEDIATES THEREFOR

BACKGROUND OF THE INVENTION

The present invention is related to cis-C$_3''$,C$_4''$-carbonate derivatives of oleandomycin-Y(O-demethyloleandomycin), the pharmaceutically-acceptable acid addition salts thereof and synthetic intermediates therefor.

Oleandomycin, in the form of its triacetate ester (troleandomycin) is well established as an antibacterial agent in the medicinal art. In the fermentation of oleandomycin, a byproduct is oleandomycin-Y having the formula

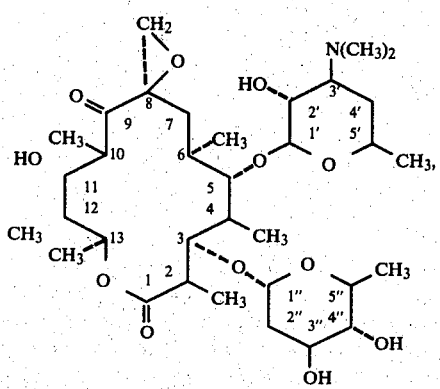

also known as O-demethyloleandomycin. This byproduct, because of its relatively low antibacterial activity, has heretofore not found applicability in the medicinal art. Now, through a series of chemical reactions it has been possible to convert oleandomycin-Y to cis-carbonate derivatives having an unexpectedly enhanced level of antibacterial activity.

SUMMARY OF THE INVENTION

The compounds of the present invention are cis-C''$_3$,C$_4''$-carbonate derivatives of oleandomycin-Y. These novel compounds have the formulae

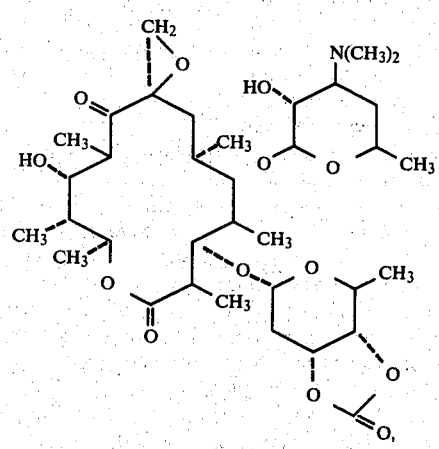

and

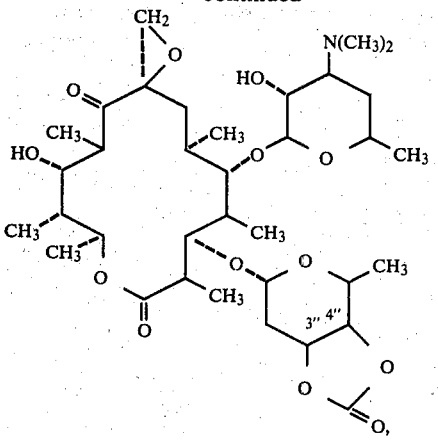

Named as oleandomycin-Y derivatives, they are respectively 3''-epioleandomycin-Y 3'',4''-carbonate(IIa) and 4''-epioleandomycin-Y 3'',4''-carbonate. As a matter of convenience the mixture of these two compounds is referred to as oleandomycin-Y cis-C$_3''$,C$_4''$-carbonates.

Unexpectedly, the two cis-carbonate products of the present invention have much enhanced antibacterial activity over oleandomycin-Y. The antibacterial activity of these compounds is readily determined by standard methods of serial dilution or disc-plate as described in greater detail below. The latter method in particular is routinely applied to check the susceptibility of microorganisms, including those freshly isolated in clinical practice. The measured antibacterial activity reflects utility in the systemic or topical treatment of animal or human infections due to susceptible bacteria, in animal feeds as growth promotants, in the preservation of substances biogradable by susceptible bacteria or as industrial disinfectants.

The pharmaceutically acceptable acid addition salts of this invention include, but are not limited to, those formed with hydrochloric, hydrobromic, nitric, phosphoric, sulfuric, benzenesulfonic citric, laurylsulfonic fumaric, oxalic, maleic, methanesulfonic, p-toluenesulfonic and succinic acid.

The present invention also encompasses the processes and more particularly the synthetic intermediates as detailed in the Flowsheet. In this flowsheet it will be evident that the diagrammatic

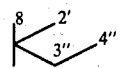

is used as a short-hand form designating the 8, 2', 3'' and 4'' positions of the oleandomycin-Y nucleus. As oleandomycin-Y derivatives, these intermediates are conveniently and unambiguously named as follows:

III 2'-acyloleandomycin-Y;
IV 2'-acyl-8-de(spirooxiranyl)-8-iodomethyl-8-hydroxy-3'',4''-anhydro-3''-deoxyoleandomycin-Y;
V 2'-acyl-3'',4''-anhydro-3''-deoxyoleandomycin-Y;
VIa 2'-acyl-3''-epioleandomycin-Y;
VIb 2'-acyl-4''-epioleandomycin-Y;
VIIa 2'-acyl-3''-epioleandomycin-Y 3'',4''-carbonate, and
VIIb 2'-acyl-4''-epioleandomycin-Y 3'',4''-carbonate.

Preferred intermediates are those wherein R is methyl, since these compounds are particularly readily prepared and carried through the reaction sequence.

Flowsheet

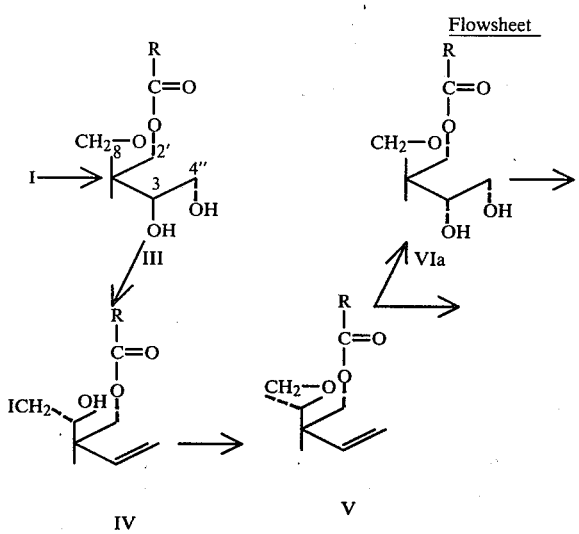
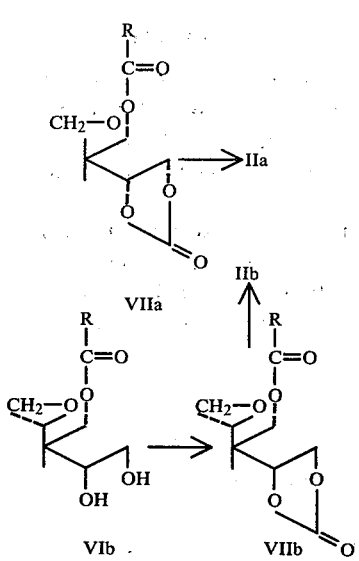

R = H, (C₁-C₅)alkyl, phenyl or benzyl.

DETAILED DESCRIPTION OF THE INVENTION

The oleandomycin-Y derivatives of the present invention are prepared by a sequence of chemical reactions, as summarized in the Flowsheet.

As the first stage, the 2'-hydroxyl group of oleandomycin-Y is selectively acylated. This acylation is conveniently carried out by reacting oleandomycin-Y with 1 to 1.1 equivalents of the appropriate acid anhydride (e.g. acetic anhydride, propionic anhydride, benzoic anhydride) or mixed acid anhydride (e.g. acetic formic anhydride, acetic p-toluenesulfonic anhydride, phenylacetic ethylchloroformic anhydride) under mild temperature conditions (e.g. 0°–35° C.) in a reaction inert solvent (e.g. ethyl acetate, methylene chloride). The resulting intermediate (III) can be carried in situ into the next step, but is generally isolated in the free base form by standard extraction techniques.

The second stage (III–IV) of the sequence involves conversion of the 3",4"-glycol to the 3"-ene with simultaneous opening of the epoxide to form the iodohydrin under the reaction conditions. This transformation is accomplished by reacting the 2'-acyloleandomycin-Y with substantially 1.6–2 equivalents of 2,4,5-triodoimidazole, 2 equivalents of imidazole and 3 equivalents of triphenylphosphine in a reaction inert solvent (e.g. an aromatic hydrocarbon) at a temperature of 90°–130° C. (conveniently, the reflux temperature of the reaction mixture if the solvent employed is toluene). If the isolation of iodohydrin is desired the reaction mixture is carefully extracted with water and evaporated to dryness. If desired, the product is purified by chromatography on a neutral absorbant. During isolation, the exposure of the product to base is avoided in view of the facile recyclization of the iodohydrin to epoxide in the presence of a basic catalyst. It is generally preferred to in fact expose reaction product to base during isolation (e.g. in the form of aqueous sodium bicarbonate, or basic activated alumina employed for chromatography) thus readily accomplishing the third stage of the overall process, IV→V, reformation of the epoxide.

If desired, intermediate V is purified by chromatography. However, such purification is not essential to the over-all process and it is more efficient to simply carry relatively unstable intermediate in freshly prepared crude form, or in situ, into the fourth stage of the process, conversion of the 3"-ene to the cis-glycols (VIa and VIb). The latter transformation is accomplished by reaction of intermediate V with excess of a tertiary aliphatic amine N-oxide (e.g. 4–6 molar equivalents of N-methylmorpholine N-oxide) and osmium tetroxide (0.05–0.15 molar equivalents) in an aqueous and/or alcoholic solvent (e.g. aqueous tert-butanol) at a temperature of 0°–50° C. (conveniently ambient temperature). The reaction mixture is treated with sodium bisulfite (e.g. about 3 molar equivalents) prior to isolation by standard extraction techniques. If desired, the resulting cis-glycols (VIa and VIb) can be separated by column chromatography. It is preferred, however, to simply carry the mixture into the next stage of the over-all process.

The fifth stage of the over-all process is the formation of 3",4"cyclic carbonate (VIa→VIIa; VIb→VIIb). Carbonate ester formation is readily accomplished by reaction of the glycol with an activated form of carbonic acid (phosgene, 1,1'-carbonyldiimidazole, etc.). There being no acid byproduct, a reagent such as 1,1'-carbonyldiimidazole is particularly convenient, usually in moderate excess (e.g. 1.1–1.5 molar equivalents) in a reaction inert solvent (e.g. methylene chloride) at 0°–50° C. (conveniently ambient temperature). The product is isolated by standard extraction techniques.

The final stage of over-all process is selective removal of the acyl protecting group introduced in the first stage. This is readily accomplished by solvolysis in methanol under mild conditions of temperature (e.g. 0°–50° C. conveniently ambient temperature). The desired products (IIa and IIb) are readily isolated by simple evaporation. If not previously separated, the two cis isomers can be separated by chromatography.

The pharmaceutically-acceptable acid addition salts of IIa are IIb are readily prepared by contacting the free base with a molar equivalent of the appropriate mineral or organic acid in an aqueous or organic solvent. If the salt directly precipitates, it is simply recovered by filtration. Otherwise it is isolated by concentration and/or addition of a non-solvent.

The antibacterial activity of the compounds of the formulae IIa and IIb was demonstrated by measuring their minimum inhibitory concentrations (MIC's) in mcg./ml. against a variety of microorganisms. The procedure which is followed is the one recommended by the International Collaborative Study on Antibiotic Sensitivity Testing [Ericcson and Sherris, Acta. Pathologica et Microbiologia Scandinav, Supp. 217, Sections A and B: 64-68 (1971)], and employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye. A comparison of the activity of 3''-epioleandomycin-Y 3'',4''-carbonate and 4''-epioleandomycin-Y 3'',4''-carbonate with that of parent oleandomycin-Y is recorded in the Table.

TABLE

Antibacterial Activity of Oleandomycin-Y(I) 3''-Epioleandomycin-Y(IIa) 3'',4''-carbonate and 4''-Epioleandomycin-Y(IIb) 3'',4''-carbonate

| Microorganism | Minimum Inhibitory Concentration (MIC) mcg./ml. | | |
|---|---|---|---|
| | (I) | (IIa) | (IIb) |
| Staph. aur. 5 | 50 | 3.12 | 12.5 |
| Staph. aur. 52 | 50 | 3.12 | 12.5 |
| Staph. aur. 400 | 12.5 | 6.25 | 12.5 |
| Staph. epi. 111 | 6.25 | 1.56 | 6.25 |
| Strep. faec. 6 | 6.25 | 3.12 | 12.5 |
| Strep. pneum. 2 | 0.78 | 0.39 | 0.78 |
| Strep. pyog. 203 | 1.56 | 3.12 | 3.12 |
| Bac. sub. 1 | 6.25 | 0.78 | 3.12 |
| Past. mult. | — | 50 | — |

For the treatment of systemic infections in animals, including man, caused by susceptible microorganisms, compounds IIa and IIb are dosed at a level of 2.5–100 mg./kg. per day, preferably 5–50 mg./kg./day, usually in divided doses. Variation in dosage will be made depending upon the individual and upon the susceptibility of the microorganisms. These compounds are dosed orally or parenterally. The susceptibility of microorganisms isolated in the clinics is routinely tested in clinical laboratories by the well-known disc-plate method. The preferred compound is that which shows the largest diameter zone of inhibition against the bacteria causing the infection to be treated.

Preparation of optimal dosage forms will be by methods well known in the pharmacists art. For oral administration, the compounds are formulated alone or in combination with pharmaceutical carriers such as inert solid diluents, aqueous solutions or various non-toxic organic solvents in such dosage forms as gelatin capsules, tablets, powders, lozenges, syrups and the like. Such carriers include water, ethanol, benzyl alcohol; glycerin, propylene glycol, vegetable oils, lactose, starches, talc, gelatins, gums and other well known carriers. The parenteral dosage forms required for the above systemic use are dissolved or suspended in a pharmaceutically-acceptable carrier such as water, saline, sesame oil and the like. Agents which improve the suspendability and dispersion qualities can also be added.

For the topical treatment of superficial infections in animals, including man, caused by susceptible microorganisms, the cis-carbonate compounds are formulated by methods well known in the pharmacist's art into lotions, ointments, creams, salves, gels, or the like at concentrations in the range 5–200 mg./cc. of the dosage form, preferably in the range 10–100 mg./cc. The dosage form is applied at the site of infection ad libitum, generally at least once a day.

When the antibacterial compounds of the present invention are used as preservatives of biodegradable materials, they are simply blended with the biodegradable material at a concentration which is at least sufficient to inhibit the growth of the bacteria causing biodegradation. Routine serial dilution techniques can be used to determine the concentrations necessary to achieve the desired purpose.

When the antibacterial compounds of the present invention are used as growth promotants in domestic food animals, they are provided at low levels (e.g. 10 g. to 100 g. of compound per ton of feed). Blending of the compound with feed is usually accomplished in two stages, first in the preparation of a preblend (e.g. 10–100 g. of compound blended with 10–20 lb. of soybean mill run or the like), which is then blended with the feed at the time of milling.

When these compounds are used as industrial disinfectants, they are generally applied as dilute solutions to the surfaces which are to be disinfected.

The present invention is illustrated by the following examples. However, it should be understood that the invention is not limited to the specific details of these examples.

EXAMPLE 1

Oleandomycin Y (I)

Oleandomycin-Y is typically a 2–10% byproduct in the fermentation of oleandomycin. The procedure to separate oleandomycin-Y from oleandomycin was as follows: 200.0 g. of a typical oleandomycin fermentation batch was dissolved in a mixture of 800 ml. of CHCl$_3$ and 700 ml. of H$_2$O. The pH of the solution was adjusted to 5.2 with 6 N HCl. The CHCl$_3$ layer was separated from this aqueous layer, and to the aqueous layer was added an additional 300 ml. of CHCl$_3$. The pH of this solution was readjusted to 5.5 with 20% NaOH. The CHCl$_3$ layer was then separated from the aqueous layer. This procedure was repeated three times, or until the thin layer chromatogram indicated all of the oleandomycin had been removed. The pH of the aqueous layer was then adjusted to 9.5 with the NaOH and extracted 3 times with 300 ml. of ethyl acetate. The ethyl acetate was dried (Na$_2$SO$_4$) and evaporated under reduced pressure to yield 14.0 g. (7%) of oleandomycin-Y. Rf (5:1/CHCl$_3$:MeOH)=0.15.

EXAMPLE 2

2'-Acetyloleandomycin-Y (III, R=CH$_3$)

A mixture of 1.2 g. (0.0018 m) of oleandomycin-Y and 0.19 (0.002 m) of acetic anhydride was stirred in 20 ml. of ethylacetate at room temperature for 4 hrs. To this solution was added 50 ml. of water and the pH adjusted to 9.5. The ethyl acetate was separated from the aqueous layer, dried (Na$_2$SO$_4$) and evaporated to yield 1.0 g. of 2'-acetyloleandomycin-Y (77% yield) as a white amorphous foam. NMR (CDCl$_3$) delta 5.55 (q, 1H), 2.26 (s, 6H), 2.05 (s, 3H). TLC(3:1 CHCl$_3$: CH$_3$OH) Rf=0.60.

Analysis Calcd. for C$_{36}$H$_{61}$O$_{13}$N.H$_2$O: C, 58.91; H, 8.65; N, 1.91. Found: C, 59.00; H, 8.46, N, 2.07.

Substituting an equivalent of acetic formic anhydride [as "acetoformic acid reagent"; cf Blackwood et al. J. Am. Chem. Soc. 82, pp. 5194–7 (1960)] for acetic anhydride, the corresponding 2'-formyloleandomycin-Y (III, R=H) is prepared.

Substituting other suitable acid anhydrides or mixed anhydrides for acetic anhydride, the following additional esters are prepared:

2'-propionyloleandomycin-Y (III, R=CH$_3$CH$_2$);
2'-isobutyryloleandomycin-Y [III, R=CH$_3$CH(CH$_3$)];
2'-isovaleryloleandomycin-Y [III, R=CH$_3$CH(CH$_3$)CH$_2$];
2'-hexanoyloleandomycin-Y [III, R=CH$_3$(CH$_2$)$_4$];
2'-benzoyloleandomycin-Y (III, R=C$_6$H$_5$); and
2'-phenylacetyloleandomycin-Y (III, R=C$_6$H$_5$CH$_2$).

EXAMPLE 3

2'-acetyl-8-de(spirooxiranyl)-8-iodomethyl-8-hydroxy-3'',4''-anhydro-3''-deoxyoleandomycin-Y (IV, R=CH$_3$)

A mixture of 0.25 g. (0.00035 m) of 2'-acetyloleandomycin-Y, 0.25 g. (0.00056 m) of triiodoimidazole, 0.048 g. (0.0007 m) of imidazole and 0.37 g. (0.0014 m) of triphenylphosphine was refluxed in 10 ml. of toluene for 1.5 hr. The solution was poured into H$_2$O, the toluene layer separated and dried (Na$_2$SO$_4$) and the toluene evaporated to yield a white amorphous solid. This solid was dissolved in CHCl$_3$, and placed on a 7 g. column of silica gel, using 1:1 CHCl$_3$/acetone as eluant. The appropriate fractions were combined and evaporated to yield 0.06 g. (22%) of the title product. NMR (CDCl$_3$) delta 5.60 (m, 2H, C$_3$''-C$_4$'') 5.55 (q, 1H, C$_{13}$H) 3.46 (s, 2H, CH$_2$I) 2.30 (s, 6H, N(CH$_3$)$_2$) 2.01 (s, 3H, COCH$_3$). Mass spectrum: 497.1401 calculating for C$_{20}$H$_{34}$O$_6$I(±0.0 pgm) aylycone; 200.1270 (±1.6 ppm; base peak) and 140.1046 (±2.4 ppm) desosamine sugar; 97.0702 calculating for C$_6$H$_9$O (±4.8 ppm) C$_3$'', C$_4$'' dehydro oleandrose. Rf (1:1 CHCl$_3$: acetone)=0.50.

By the same method, the other esters of the preceding example are converted to:

2'-formyl-8-de(spirooxiranyl)-8-iodomethyl-8-hydroxy-3'',4''-anhydro-3''-deoxyoleandomycin-Y (IV, R=H);
2'-propionyl-8-de(spirooxiranyl)-8-iodomethyl-8-hydroxy-3'',4''-anhydro-3''-deoxyoleandomycin-Y (IV, R=CH$_3$CH$_2$);
2'-isobutyryl-8-de(spirooxiranyl)-8-iodomethyl-8-hydroxy-3'',4''-anhydro-3''-deoxyoleandomycin-Y [(IV, R=CH$_3$CH(CH$_3$)];
2'-isovaleryl-8-de(spirooxiranyl)-8-iodomethyl-8-hydroxy-3'',4''-anhydro-3''-deoxyoleandomycin-Y [(IV, R=CH$_3$CH(CH$_3$)CH$_2$];
2'-hexanoyl-8-de(spirooxiranyl)-8-iodomethyl-8-hydroxy-3'',4''-anhydro-3''-deoxyoleandomycin-Y [(IV, R=CH$_3$(CH$_2$)$_4$];
2'-benzoyl-8-de(spirooxiranyl)-8-iodomethyl-8-hydroxy-3'',4''-anhydro-3''-deoxyoleandomycin-Y (IV, R=C$_6$H$_5$); and
2'-phenylacetyl-8-de(spirooxiranyl)-8-iodomethyl-8-hydroxy-3'',4''-anhydro-3''-deoxyoleandomycin-Y (IV, R=C$_6$H$_5$CH$_2$).

EXAMPLE 4

2'-Acetyl-3'',4''-anhydro-3'-deoxyoleandomycin-Y (V, R=CH$_3$)

A mixture of 2'-acetyloleandomycin-Y, 0.37 g. (0.00052 m) of imidazole, 0.64 g. (0.0014 m)) of triiodoimidazole and 0.15 g. (0.0021 m) of triphenylphosphine was refluxed for 1 hr. in 15 ml. of toluene. The solution was cooled to room temperature and the solvent evaporated. The residue was dissolved in CHCl$_3$ and chromatographed on 15 g. of Woelm basic alumina (activity 1) using 1:1/CHCH$_3$: hexane as the eluant. Appropriate fractions were combined to yield 0.1 g. (21%) of the title product as an amorphous white foam. TLC Rf (1:1 EtOAc:acetone)=0.37. NMR (CDCl$_3$) delta 5.13 (m, 2H, C$_3$'', C$_4$''H) 5.55 (q, l, C$_{13}$H) 2.86, 2.80 (2H, C$_8$ epoxide methylene) 2.26 (s, 6H, N(CH$_3$)$_2$) 2.05 (s, 3H, COCH$_3$).

By the same procedure the other esters of Example 2 are converted to:

2'-formyl-3'',4''-anhydro-3''-deoxyoleandomycin-Y (V, R=H);
2'-propionyl-3'',4''-anhydro-3''-deoxyoleandomycin-Y (V, R=CH$_3$CH$_2$);
2'-isobutyryl-3'',4''-anhydro-3''-deoxyoleandomycin-Y [V, R=CH$_3$CH(CH$_3$)];
2'-isovaleryl-3'',4''-anhydro-3''-deoxyoleandomycin-Y [V, R=CH$_3$CH(CH$_3$)CH$_2$];
2'-hexanoyl-3'',4''-anhydro-3''-deoxyoleandomycin-Y [V, R=CH$_3$(CH$_2$)$_4$];
2'-benzoyl-3'',4''-anhydro-3''-deoxyoleandomycin-Y (V, R=C$_6$H$_5$); and
2'-phenylacetyl-3'',4''-anhydro-3''-deoxyoleandomycin-Y (V, R=C$_6$H$_5$CH$_2$).

EXAMPLE 5

2'-Acetyl-3''-epioleandomycin-Y (VIa, R=CH$_3$) and 2'Acetyl-4''-epioleandomycin-Y (VIb, R=CH$_3$)

A mixture of 4.0 g. (0.0056 m) of 2'-acetyloleandomycin-Y, 4.0 g. (0.009 m) of triiodoimidazole, 0.76 g. (0.0112 m) of imidazole and 4.4 g (0.0168 m) of triphenylphosphine was refluxed in 400 ml. of toluene for 4 hrs. The solution was cooled to ambient temperature, washed with saturated NaHCO$_3$, 5% sodium thiosulfate, and saturated brine. The organic layer was dried and the toluene evaporated to yield a yellow amorphous foam. This residue was dissolved in 50 ml. of acetone and to the solution was added succesively 3.4 g. (0.025 m) N-methylmorpholine N-oxide, 0.125 g. (0.000492 m) of OsO$_4$ dissolved in 25 ml. of t-butanol, and 50 ml. of water. The solution was stirred 3 hrs. at room temperature after which 1.5 g. (0.014 m) of sodium bisulfite was added. Stirring was continued for 15 minutes, and the mixture was filtered. The filtrate was diluted with 100 ml. of H$_2$O, the pH adjusted to 8.5, and extracted with 3×50 ml. of ethyl acetate. The ethyl acetate layer was recombined with 100 ml. of H$_2$O and the pH adjusted to 2.5. The ethyl acetate layer was separated and the pH of the H₂O was adjusted to 4.0. The aqueous layer was reextracted with ethylacetate (1×50 ml.) and the aqueous layer was then adjusted to pH 9.0. The aqueous layer was again extracted with ethyl acetate. This ethyl acetate layer was dried and evaporated to yield 1.1 g. (28% yield) of a mixture of the title products as a white amorphous foam. TLC (5:1 CHCl₃: MeOH) Rf=0.32, 0.38. NMR (CDCl₃) delta 5.61 (q, 1H, C₁₃H) 2.80, 2.70 (2H, C₁ epoxide methylene) 2.25 (s, 6H, N(CH₃)₂) 2.05 (s, 3H, COCH₃). Mass spectrum: 369.2269, 351.2159 aglycone residues; 200.1287 and 140.1072 desosamine residue; 131.0708 indicating C₆H₁₁O₃ (±0.6 ppm) and 113.0608 indicating C₆H₉O₂ (±0.6 ppm) neutral sugar fragmentation.

By the same method the other esters of Example 2 are converted to:

2'-formyl-3"-epioleandomycin-Y (VIa, R=H);
2'-formyl-4"-epioleandomycin-Y (VIb, R=H);
2'-propionyl-3"-epioleandomycin-Y (VIa, R=CH₃CH₂);
2'-propionyl-4"-epioleandomycin-Y (VIb, R=CH₃CH₂);
2'-isobutyryl-3"-epioleandomycin-Y [(VIa, R=CH₃CH(CH₃)];
2'-isobutyryl-4"-epioleandomycin-Y [VIb; R=CH₃CH(CH₃)];
2'-isovaleryl-3"-epioleandomycin-Y [VIa, R=CH₃CH(CH₃)CH₂];
2'-isovaleryl-4"-epioleandomycin-Y [VIb, R=CH₃CH(CH₃)CH₂];
2'-hexanoyl-3"-epioleandomycin-Y [VIa, R=CH₃(CH₂)₄];
2'-hexanoyl-4"-epioleandomycin-Y [VIb, R=CH₃(CH₂)₄];
2'-benzoyl-3"-epioleandomycin-Y (VIa, R=C₆H₅);
2'-benzoyl-4"-epioleandomycin-Y (VIb; R=C₆H₅);
2'-phenylacetyl-3"-epioleandomycin-Y (VIa, R=C₆H₅CH₂); and
2'-phenylacetyl-4"-epioleandomycin-Y (VIb, R=C₆H₂CH₂).

EXAMPLE 6

2'-Acetyl-3"-epioleandomycin-Y 3",4"-Carbonate (VIIa, R=CH₃) and 2'-Acetyl-4"-epioleandomycin-Y 3",4"-Carbonate (VIIb, R=CH₃)

A mixture of 2'-acetyl-3"-epioleandomycin-Y and 2'-acetyl-4"-epioleandomycin-Y from the preceding example (0.8 g. 0.00112 m), and 0.37 g. (0.00140 m) of 1,1'-carbonyldiimidazole was stirred in 10 ml. of CH₂Cl₂ at room temperature for 3 hrs. The solution was washed with 50 ml. H₂O and 50 ml. of saturated brine. The organic layer was dried and evaporated to yield a mixture of the title products as a white amorphous solid. TLC (1:1/CHCl₃:acetone) Rf=0.65.

By the same process the other esters of the preceding example are converted to:

2'-formyl-3"-epioleandomycin-Y 3",4"-carbonate (VIIa, R=H);
2'-formyl-4"-epioleandomycin-Y 3",4"-carbonate (VIIb, R=H).
2'-propionyl-3"-epioleandomycin-Y 3",4"-carbonate (VIIa, R=CH₃CH₂);
2'-propionyl-4"-epioleandomycin-Y 3",4"-carbonate (VIIb, R=CH₃CH₂);
2'-isobutyryl-3"-epioleandomycin-Y 3",4"-carbonate [(VIIa, R=CH₃CH(CH₃)];
2'-isobutyryl-4"-epioleandomycin-Y 3",4"-carbonate [(VIIb, R=CH₃CH(CH₃)];
2'-isovaleryl-3"-epioleandomycin-Y 3",4"-carbonate [VIIa, R=CH₃CH(CH₃)CH₂];
2'-isovaleryl-4"-epioleandomycin-Y 3",4"-carbonate [VIIb, R=CH₃CH(CH₃)CH₂];
2'-hexanoyl-3"-epioleandomycin-Y 3",4"-carbonate [VIIa, R=CH₃(CH₂)₄];
2'-hexanoyl-4"-epioleandomycin-Y 3",4"-carbonate [VIIb, R=CH₃(CH₂)₄];
2'-benzoyl-3"-epioleandomycin-Y 3",4"-carbonate (VIIa,, R=C₆H₅);
2'-benzoyl-4"-epioleandomycin-Y 3",4"-carbonate (VIIb, R=C₆H₅);
2'-phenylacetyl-3"-epioleandomycin-Y 3",4"-carbonate (VIIa, R=C₆H₅CH₂); and
2'-phenylacetyl-4"-epioleandomycin-Y 3",4"-carbonate (VIIb, R=CH₆H₅CH₂).

EXAMPLE 7

2"-Epioleandomycin-Y 3",4"-Carbonate (IIa) and 4"-Epioleandomycin-Y 3",4", Carbonate (IIb)

A mixture of 2'-acetyl-3"-epioleandomycin 3",4"-carbonate and 2'acetyl-4"-epioleandomycin 3",4"-carbonate (the entire batch of amorphous product from the preceding example) was dissolved in 30 ml. of CH₃OH and stirred at room temperature for 48 hrs. Evaporation of the solvent gave a white amorphous solid which was chromatographed on 15 g. of silica gel using 3:2- EtOAc: acetone as the eluant. Combination of appropriate fractions yielded 0.12 g. of 3"-epioleandomycin-Y 3",4"-carbonate in which the C₃"-oxygen is in the axial orientation (trans to the C₅"methyl). 270 MHZ NMR (CDCl₃), delta 5.55 (q., J=7 Hz, 1H, C₁₃H) 4.99 (ddd, 1H, C₁") 4.78 (m, 1H, C₃") 4.31 (dd, 1H, C₄") 4.02 (dq, 1H, C₅"), 2.32 (s, 6H, N(CH₃)₂) 1.38 (d, 3H, C₆"). Upon irradiation of delta 4.78, C₄" collapses to dd J=7 Hz indicating the proton is equatorial (cis to the C₅"-methyl group). This establishes the orientation of the C₃"C₄"-carbonate. TLC (5:1/CHCl₃/MeOH) Rf=0.6. Further elution of the column gave 0.10 g. of 4"-epioleandomycin-Y 3",4"-carbonate in which the C₃"-oxygen is in the equatorial orientation (cis to the C₅" methyl). NMR (CDCl₃) delta 5.6 (q, 1H, C₁₃H) 2.30 (s, 6H, N(CH₃)₂). TLC (5:1/CHCl₃:CH₃OH) Rf=0.5.

By the same method the other esters of the preceding example are converted to the same products.

I claim:

1. A compound selected from the group consisting of 3"-epioleandomycin-Y 3",4"-carbonate, 4"-epioleandomycin-Y 3",4"-carbonate and the pharmaceutically acceptable salts thereof.

2. The compound of claim 1 which is 3"-epioleandomycin-Y 3",4"-carbonate.

3. The compound of claim 1 which is 4"-epioleandomycin-Y 3",4"-carbonate.

4. A compound selected from the group consisting of 2'acyl ester derivatives of 8-de(spirooxiranyl)-8-iodomethyl-8-hydroxy-3",4"-anhydro-3"-deoxyoleandomycin-Y wherein said acyl functionality is RCO— and R is hydrogen, (C₁–C₅)alkyl, phenyl or benzyl.

5. The compound of claim 4 wherein R is methyl.

6. A compound selected from the group consisting of 2'-acyl ester derivatives of 3",4"-anhydro-3"-deoxyoleandomycin-Y wherein said acyl functionality is RCO— and R is hydrogen, (C₁–C₅)alkyl, phenyl or benzyl.

7. The compound of claim 6 wherein R' is methyl.

8. A compound selected from the group consisting of 2'-acyl ester derivatives of 3''-epioleandomycin-Y and 2'-acyl ester derivatives of 4''-epioleandomycin, wherein said acyl functionality is RCO— and R is hydrogen, $(C_1-C_5)$alkyl, phenyl or benzyl.

9. The compound of claim 8 which is 2'-acetyl-3''-epioleandomycin-Y.

10. The compound of claim 8 which is 2'-acetyl-4''-epioleandomycin-Y.

11. A compound selected from the group consisting of 2'-acyl ester derivatives of 3''-epioleandomycin-Y 3'',4''-carbonate and 2'-acyl ester derivatives of 4''-epioleandomycin-Y 3'',4''-carbonate wherein said acyl functionality is RCO— and R is hydrogen, $(C_1-C_5)$alkyl, phenyl or benzyl.

12. The compound of claim 11 which is 2'-acetyl-3''-epioleandomycin-Y 3'',4''-carbonate.

13. The compound of claim 11 which is 2'-acetyl-4''-epioleandomycin-Y 3'',4''-carbonate.

* * * * *